(12) United States Patent
Schnatterer et al.

(10) Patent No.: US 6,365,780 B1
(45) Date of Patent: Apr. 2, 2002

(54) PROCESS FOR THE PREPARATION OF AROMATIC OR HETEROAROMATIC SULPHONYL CHLORIDES

(75) Inventors: Albert Schnatterer, Leverkusen; Monika Hermann, Rösrath, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/384,325

(22) Filed: Aug. 27, 1999

(30) Foreign Application Priority Data

Sep. 4, 1998 (DE) .......................... 198 40 319

(51) Int. Cl.⁷ ...................... C07C 317/14; C07C 309/86
(52) U.S. Cl. .................... 568/28; 546/294; 546/153; 568/32
(58) Field of Search ............... 564/305; 568/32, 568/24, 28; 546/294

(56) References Cited

U.S. PATENT DOCUMENTS

| 3,947,512 A | | 3/1976 | Gengnagel et al. | ......... 562/828 |
| 4,393,211 A | * | 7/1983 | Tonne et al. | ......... 546/153 |
| 4,457,875 A | * | 7/1984 | Fournier et al. | ........... 562/833 |
| 4,618,459 A | * | 10/1986 | Fournier et al. | ........... 562/833 |

OTHER PUBLICATIONS

L.G.Wade Jr. "Organic Chemistry," pp. 941–943, Prentice–Hall,Inc. 1987.*
Chem. Ber. 90, (month anavailable) 1957, pp. 841–852.

* cited by examiner

*Primary Examiner*—Alan L. Rotman

(74) *Attorney, Agent, or Firm*—Joseph C. Gil; Diderico van Eyl

(57) ABSTRACT

Aromatic or heteroaromatic sulphonyl chlorides of the general formula I

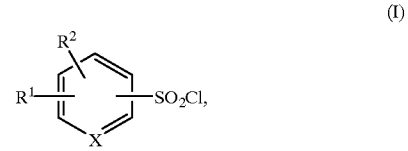

(I)

in which
X may be a C or N,
R¹ may be fluorine, chlorine, bromine, nitro, methoxy, fluoromethoxy, difluoromethoxy, trifluoromethoxy, $C_1$–$C_4$ alkyl or phenyl,
R² may be H, fluorine, chlorine, bromine, OH, $C_1$–$C_4$ alkyl, are prepared by diazotization of the compounds of the general formula II

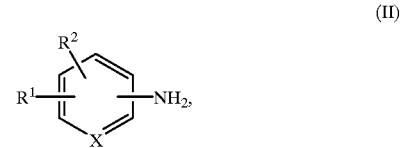

(II)

in which
X, R¹ and R² are as defined for formula (I), and decomposition of the resulting diazonium salts in the presence of sulphur dioxide and a copper catalyst, where the compounds of the formula (II) are treated, in a mixture with one or more organic solvents, sulphur dioxide and a copper catalyst, with hydrogen chloride and alkyl nitrite at temperatures of from −20 to +60° C.

12 Claims, No Drawings

PROCESS FOR THE PREPARATION OF AROMATIC OR HETEROAROMATIC SULPHONYL CHLORIDES

FIELD OF THE INVENTION

The present invention relates to a process for the preparation of aromatic or heteroaromatic sulphonyl chlorides by diazotization of amino-substituted aromatics or heteroaromatics and decomposition of the resulting diazonium salts in the presence of sulphur dioxide.

BACKGROUND OF THE INVENTION

Aromatic sulphonyl chlorides are important intermediates for crop-protection products, pharmaceuticals and dyes. From Chem. Ber. 90, 1957, p. 841, it is known to prepare this class of compound by diazotization of the corresponding aromatic amines with aqueous sodium nitrite solutions and decomposition of the diazonium salts in solutions of sulphur dioxide, copper salts and acetic acid. Where appropriate, a water-immiscible organic solvent is also added so that the reaction mixture is two-phase. This process does, however, have a number of disadvantages. For example, the yields are unsatisfactory in many cases. While electron-withdrawing groups, as further substituents in the diazonium salts, have a favourable effect on the yield and the reaction rate, the use of diazonium salts, which carry electron-donating substituents, leads only to low yields. In addition, when the reaction is carried out on an industrial scale, large amounts of wastewater which contains copper and acetic acid are formed. The processing and disposal of such wastewater is costly and is not possible using an economic process. If diazonium salts containing electron-withdrawing substituents on the aromatic ring are used, such as dinitrobenzenediazonium chlorides, it is in some circumstances also possible to carry out the process without the copper salts as catalyst. Although the yields in this case are not much lower than in the presence of the catalyst, the reaction rate does drop considerably.

German Offenlegungsschrift 2,308,262 discloses a further process for the preparation of aromatic sulphonyl chlorides in which the sulphur dioxide is used in the form of alkali metal hydrogen sulphite in the presence of copper or copper salts. The addition of acetic acid or other organic solvents is not necessary here, the aromatic diazonium salts are used in strong hydrochloric acid solution. According to EP-A-0,059, 241, the reaction of the aqueous diazonium salt solution with sulphur dioxide is carried out in the presence of a solvent which is immiscible or miscible only to a limited extent with water, and copper salts as catalyst, and subsequently the reaction mixture is treated with an oxidizing agent.

Although these processes avoid the problem of wastewater containing acetic acid being produced, as a result of the diazotization of the anilines in an aqueous medium and the use of dilute aqueous diazonium salt solutions in the reaction with the sulphur dioxide in the presence of copper, large amounts of wastewater containing copper salts are again formed. Furthermore, the space-time yield of these processes is unsatisfactory as a result of the use of dilute aqueous diazonium salt solution and the large volumes which arise as a result. In addition, the handling of the diazonium salt solutions requires specific precautionary measures because of the decomposability of the diazonium salts. For example, these solutions must be handled at low temperatures around 0° C. and be processed quickly in order to limit yield losses in industrial operation.

All of the abovementioned processes have the common disadvantage that the conversion of the anilines into the corresponding aromatic sulphonyl chlorides takes place in two stages. In the first stage, the diazotization of the aniline with aqueous sodium nitrite solution takes place, and in the second stage, the decomposition of the diazonium salt in the presence of sulphur dioxide or alkali metal hydrogen sulphite, a copper compound and, where appropriate, an organic solvent.

There is therefore a need for a process which permits the preparation of aromatic or heteroaromatic sulphonyl chlorides from the parent anilines or amino-substituted pyridines in a simple manner with a high chemical yield, a high space-time yield, coupled with the formation of only a small amount of wastewater.

DESCRIPTION OF THE INVENTION

The invention provides a process for the preparation of aromatic or heteroaromatic sulphonyl chlorides of the general formula I

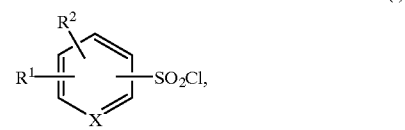

(I)

in which

X may be a C or N, $R^1$ may be fluorine, chlorine, bromine, nitro, methoxy, fluoromethoxy, difluoromethoxy, trifluoromethoxy, $C_1$–$C_4$ alkyl or phenyl, and $R^2$ may be H, fluorine, chlorine, bromine, OH or $C_1$–$C_4$ alkyl, by diazotization of the compounds of the general formula II

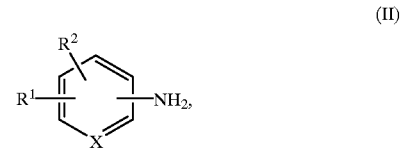

(II)

in which

X, $R^1$ and $R^2$ are as defined for formula (I), and decomposition of the resulting diazonium salts in the presence of sulphur dioxide and a copper catalyst, characterized in that the compounds of the formula (II) are treated, in a mixture with one or more organic solvents, sulphur dioxide and a copper catalyst, with hydrogen chloride and alkyl nitrite at temperatures of from −20 to +60° C.

If, in the formulae (I) and (II), $R^1$ and $R^2$ are $C_1$–$C_4$ alkyl, these alkyl radicals may be straight-chain or branched, for example, methyl, ethyl, n-propyl, isopropyl, n-butyl, isobutyl and tert-butyl may be used.

In the formulae (I) and (II), $R^1$ is preferably fluorine, chlorine, bromine, nitro, methoxy, trifluoromethoxy, methyl or ethyl, and $R^2$ is preferably hydrogen, fluorine, chlorine, bromine, methyl or ethyl.

In the formulae (I) and (II), $R^1$ is particularly preferably fluorine, chlorine, bromine, nitro or trifluoromethoxy, and $R^2$ is particularly preferably hydrogen.

If the compounds of the formula (II) are substituted anilines, i.e., X is C, the substituents $R^1$ and $R^2$ are then preferably in the 2- and/or 4-position relative to the amino radical. If the compounds of the formula (II) are substituted amino-pyridines, i.e., X is N, then the amino radical is preferably in the 3-position, and the substituents $R^1$ and $R^2$ are preferably in the 2- and/or 6-position.

Specific examples of compounds of the formula (II) on which the process of the invention can be used advantageously are 2-nitroaniline, 4-nitroaniline, 2-trifluoromethoxyaniline and 3-amino-2-chloropyridine. These compounds are available commercially.

Suitable organic solvents for the process of the invention are those which are essentially inert under the reaction conditions and at least partly dissolve the starting materials of the formula (I), sulphur dioxide, hydrogen chloride and the copper catalyst. Examples of such solvents are aromatic hydrocarbons, alcohols, ethers, halogenated hydrocarbons, sulphoxides and sulphones. Such solvents can be used individually or as mixtures of two or more solvents.

Preference is given to using aromatic hydrocarbons, for example, toluene, xylene, ethyl benzene, halogenated hydrocarbons, such as methylene chloride, 1,2-dichloroethane, chlorobenzene or dichlorobenzene, alcohols, such as methanol, ethanol, 1-propanol, 2-propanol, isomeric butanols, isomeric pentanols or isomeric hexanols, or ethers, such as methyl tert-butyl ether, tetrahydrofuran, ethylene glycol dimethyl ether, diethylene glycol dimethyl ether, triethylene glycol dimethyl ether or polyethylene glycol dimethyl ether as solvent.

Such solvents can also be used in mixtures with water. The addition of water can in some cases favour the solubilities of the starting materials. Here, it is insignificant whether such mixtures form one or two liquid phases. However, the addition of water is limited to small amounts of from 0.1 to 0.5 part by weight, based on the total amount of the organic solvent, depending on the process.

The amount of solvent is such that readily stirrable solutions or suspensions are obtained and, depending on its solubilizing power for the starting components, is advantageously 1–20 parts by weight, preferably 1.5–10 parts by weight, based on the compounds of the formula (II).

In order to obtain the highest possible yields of sulphonyl chlorides of the formula (I), it is expedient to use at least equimolar amounts of sulphur dioxide based on the compounds of the formula (II); it is, however, generally advisable to use a 1–8 molar, preferably 1–6-molar, particularly preferably 1.5–5 molar, excess of sulphur dioxide.

It is possible to add all of the sulphur dioxide to be used according to the invention to the reaction mixture prior to the treatment of the reaction mixture with alkyl nitrite. It can, however, also be introduced initially in partial amounts and the remainder added at the same time as the alkyl nitrite.

A suitable copper catalyst is elemental copper and also copper compounds. The copper in the copper catalyst to be used can have the valencies 0, 1, 2 or 3, preferably 1 or 2. Possible use forms are copper salts of inorganic and organic acids, for example, copper fluoride, copper chloride, copper bromide, copper sulphate, copper nitrate, and also the copper oxides, the copper salts of organic acids, such as copper acetate, copper citrate and copper stearate, and copper complexes, such as copper acetylacetonate and N,N'-disalicylidene ethylenediamine copper (II). The copper catalyst can be used in solution, preferably in alcoholic and, in particular, in methanolic, solution.

The copper catalyst is used here in an amount of 0.001–0.5 mol, preferably 0.005–0.1 mol, per mole of the compound of the formula (II).

Hydrogen chloride is expediently used in gaseous form. It can be fed in at the same time as the alkyl nitrite. It is, however, also possible to add all or some of the hydrogen chloride to the reaction mixture before the latter is treated with alkyl nitrite. The amount of hydrogen chloride is at least equimolar based on the aniline or the amino-substituted pyridine of the formula (II). Preferably, hydrogen chloride is used in an amount of 1–4 equivalents, particularly preferably 1–2 equivalents, based on the compound of the formula (II).

The alkyl nitrite used is usually methyl nitrite, ethyl nitrite or isopropyl nitrite. Preference is given to using methyl nitrite. Methyl nitrite can be prepared by reacting alkali metal nitrites with methanol in the presence of strong acids in a simple manner. Since it is gaseous under the working conditions, it is metered in as a gas at a rate which the progress of the reaction allows.

Here, the alkyl nitrite is used at least in equivalent amounts, preferably in amounts of 1–3 equivalents, particularly preferably 1–1.5 equivalents, based on the compounds of the formula (II), to achieve high yields. However, a greater excess of alkyl nitrite does not impair the result of the reaction.

The reaction temperature for the process of the invention can vary between −20 and +60° C. The process is preferably carried out at a temperature of from −10 to +40° C., particularly preferably from −10 to +30° C.

In a preferred embodiment of the process of the invention, the compound of the formula (II), the organic solvent and the copper catalyst are firstly added, then, with adjustment to a temperature in the range from −20 to +60° C., some of the hydrogen chloride and the sulphur dioxide are added, and then further hydrogen chloride and the alkyl nitrite are metered in.

The process of the invention for the preparation of aromatic or heteroaromatic sulphonyl chlorides differs from the processes known hitherto by virtue of the fact that the diazotization of the anilines or amino-substituted pyridines and the decomposition of the resulting diazonium salts are not carried out in two separate stages, but at the same time in a single stage, and by virtue of the fact that the reaction can be carried out successfully exclusively in one organic solvent or a mixture of two or more organic solvents. This results in significant advantages over the processes of the prior art: as a result of the synchronism of diazotization and decomposition of the diazonium salt, the apparatus and time expenditure for the separate preparation of the diazonium salt solutions is unnecessary. In addition, a particularly favourable space-time yield is obtained and wastewater is produced only in the form of water of reaction.

It is regarded as particularly surprising and could not have been derived from the prior art that the diazotization of the anilines or amino-substituted pyridines of the formula (II) and the simultaneous reaction of the resulting diazonium salts to give sulphonyl chlorides can be achieved in a mixture of sulphur dioxide, hydrogen chloride, copper catalyst and organic solvents in high yield. It is known from the prior art that the diazonium salt which decomposes could react with the unreacted aniline to give undesired secondary products ((Houben-Weyl, Methoden der organischen Chemie [Methods in Organic Chemistry], 4th Edition, volume X/3, page 700). This phenomenon however does not arise in the process of the invention.

The sulphonyl chlorides can be isolated from the resulting reaction mixtures very easily. If the reaction has been carried out in an organic solvent which is miscible with water to an unlimited extent, then the water of reaction separates off with the copper salt used as catalyst as its own phase. If necessary, this phase separation is induced by adding small amounts of water. The excess of sulphur dioxide and hydrogen chloride is then driven off from the organic phase which remained. The sulphonyl chloride in the organic phase can then be further converted directly, for example, to give sulphonamides by reaction with ammonia or amines.

The invention is further illustrated but is not intended to be limited by the following examples in which all parts and percentages are by weight unless otherwise specified.

EXAMPLE 1

The methyl nitrite used in the examples below was prepared as required by treating a solution of 1 part by weight of 25% strength aqueous sodium nitrite solution and 0.14 part by weight of methanol with 0.37 part by weight of 48% strength sulphuric acid, and was further processed in gaseous form.

EXAMPLE 2

A 1 l glass reactor was charged successively with 88.6 g of 2-trifluoromethoxyaniline (97.6%), 250 ml of dichloroethane and a solution of 2 g of copper (II) chloride×2 $H_2O$ in 3 ml of methanol. At a temperature of 0–10° C., 18 g of hydrogen chloride were firstly introduced into the resulting solution, followed by 128 g of sulphur dioxide. A low-viscosity suspension formed. At 0–5° C., 9 g of hydrogen chloride and 34 g of methyl nitrite were then continuously metered in simultaneously with stirring over the course of 1.5 hours. The methyl nitrite addition was accompanied by a simultaneous evolution of gas in the reaction mixture. Towards the end of the methyl nitrite addition, the suspension completely dissolved. The solution was then stirred for a further 2 hours at 5–10° C.

The excess sulphur dioxide and hydrogen chloride was then removed by distilling the reaction mixture at 20–25° C. and a pressure of 75 mbar, to leave 248 g of liquid residue, which was extracted with 50 ml of water to separate off the copper salt. Concentration by evaporation of the organic phase at 55° C. and a pressure of 40 mbar produced, as residue, 128.9 g of a slightly reddish oil with a content, determined by gas chromatography, of 91.1% of 2-trifluoromethoxy-benzenesulphonyl chloride, corresponding to a yield of 92.3% of theory.

EXAMPLE 3

A 1 l glass reactor was charged successively with 88.6 g of 2-trifluoromethoxyaniline (97.6%), 250 ml of 1,2-dimethoxyethane and a solution of 2 g of copper (II) chloride×2 $H_2O$ in 3 ml of methanol. At a temperature of 0–10° C., 18 g of hydrogen chloride were firstly introduced into the resulting solution, followed by 128 g of sulphur dioxide. After all of the sulphur dioxide was introduced, the feed mixture was in the form of a clear solution. At 0–12° C., 9 g of hydrogen chloride and 34 g of methyl nitrite were then simultaneously continuously metered in with thorough stirring over the course of 1.5 hours. The methyl nitrite addition was accompanied by a uniform formation of gas within the reaction mixture. Following the methyl nitrite addition, the solution was then stirred for a further 2 hours at 5–10° C. The reaction mixture was then concentrated by evaporation at 50° C. and 20 mbar, and the oily residue was taken up in 100 ml of 1,2-dichloroethane and extracted with 50 ml of water. Concentration of the dichloroethane phase by evaporation at 50° C. and 16 mbar produced 124.8 g of a slightly reddish oil with a content, determined by gas chromatography, of 94.6% of 2-trifluoromethoxy-benzenesulphonyl chloride as residue. The yield was 92.8% of theory.

EXAMPLE 4

A 1 l glass reactor was charged with 250 ml of toluene, 20 ml of polyethylene glycol 400, 88.6 g of 2-trifluoromethoxyaniline (97.6%) and a solution of 2 g of copper(II) chloride×2$H_2O$ in 3 ml of methanol. At 0–10° C., 27 g of hydrogen chloride were then firstly introduced into the resulting solution, followed by 128 g of sulphur dioxide, and a readily stirrable suspension formed. At 10–20° C., 34 g of methyl nitrite were then metered in continuously with vigorous stirring over the course of 1.5 hours. The methyl nitrite addition was accompanied by a uniform evolution of gas within the reaction mixture. Towards the end of the methyl nitrite addition, the suspension completely dissolved. The solution was then stirred for a further 70 minutes at 20° C.

Towards the end of the reaction, an insignificant aqueous phase separates out. Another 50 ml of water were added, the mixture was stirred vigorously, and the aqueous phase was separated off. The organic phase was concentrated by evaporation at 60° C. and 20 mbar. The residue which remained was 124.2 g of a yellow oil with a content, determined by gas chromatography, of 92.4% of 2-trifluoromethoxybenzenesulphonyl chloride. The yield was 90.2% of theory.

EXAMPLE 5

A 1 l glass reactor was charged with 69 g of 2-nitroaniline (98%), 250 ml of 1,2-dichloroethane and a solution of 2 g of $CuCl_2 \times 2H_2O$ in 3 ml of methanol. At 0–10° C., 18 g of hydrogen chloride were then firstly introduced into this mixture, followed by 128 g of sulphur dioxide, and a readily stirrable suspension formed. Then, at 0–10° C. and with vigorous stirring, 9 g of hydrogen chloride and 34 g of methyl nitrite were continuously metered in simultaneously over the course of 1.5 hours. The methyl nitrite addition was accompanied by a uniform evolution of gas in the reaction mixture. Towards the end of the methyl nitrite addition the suspension was dissolved. After all of the methyl nitrite was added, the solution was then stirred for a further 2 hours at 5–10° C. The reaction mixture was extracted with 50 ml of water, and the organic phase was concentrated by evaporation at 25° C. and 18 mbar. The residue was stirred with 150 ml of water, and the solid which had formed was drawn off with suction via a filter, washed with 50 ml of water and dried. This gives 90.3 g of a slightly brownish crystal with a content, determined by HPLC, of 91.8%. The yield was 76.4% of theory.

EXAMPLE 6

A 0.5 l glass reactor was charged with 64.7 g of 3-amino-2-chloropyridine (99.3%), 150 ml of tetrahydrofuran and 0.5 g of $CuCl_2 \times 2$ $H_2O$. At 15–20° C., 5 g of hydrogen chloride were then firstly introduced into this mixture, followed by 128 g of sulphur dioxide, and a virtually clear solution results. Then, with vigorous stirring, 18 g of hydrogen chloride and 36 g of methyl nitrite were continuously introduced simultaneously into the reaction mixture at a temperature of from −2 to +2° C. over the course of 4 hours. The methyl nitrite addition was accompanied by a uniform evolution of gas within the reaction mixture. After all of the methyl nitrite was added, the reaction solution was then stirred for a further 1.5 hours at about 0° C.

The excess of hydrogen chloride and sulphur dioxide and most of the solvent were then distilled off from the reaction mixture at 10° C. and a pressure of 30 mbar. The residue was taken up in 200 ml of toluene, and distillation was continued at 20–25° C. and a pressure of 35 mbar until most of the tetrahydrofuran and the methanol formed in the reaction have been removed. The toluenic solution which remained was extracted with 50 ml of water, and the toluenic phase was then distilled at 20° C. and 25 mbar to remove the water. This gives 181.4 g of a yellow-orange toluenic solution with a content of 47.7% of 2-chloro-3-chlorosulphonylpyridine. The yield was 81% of theory.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for the preparation of aromatic sulphonyl chlorides of the general formula I

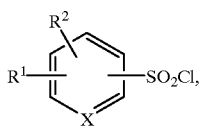

(I)

wherein

X comprises C [or N], $R^1$ comprises a component selected from the group consisting of fluorine, chlorine, bromine, nitro, methoxy groups, fluoromethoxy groups, difluoromethoxy groups, trifluoromethoxy groups, $C_1$–$C_4$ alkyl groups and phenyl groups, $R^2$ comprises a component selected from the group consisting of H, fluorine, chlorine, bromine, OH groups, and $C_1$–$C_4$ alkyl groups, by diazotization of the compounds of the general formula II

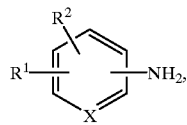

(II)

wherein

X, $R^1$ and $R^2$ are as defined for formula (I), and decomposition of the resulting diazonium salts in the presence of sulphur dioxide and a copper catalyst, wherein the compounds of the formula (II) are treated, in a mixture with one or more organic solvents, sulphur dioxide and a copper catalyst, with hydrogen chloride and alkyl nitrite at temperatures of from about –20 to +60° C.

2. Process according to claim 1, wherein, in the formulae (I) and (II), $R^1$ comprises a component selected from the group consisting of fluorine, chlorine, bromine, nitro, methoxy groups, trifluoromethoxy groups, methyl groups and ethyl groups, and wherein $R^2$ comprises a component selected from the group consisting of hydrogen, fluorine, chlorine, bromine, methyl groups and ethyl groups.

3. Process according to claim 1, wherein the anilines of the formula (I) used comprise a component selected from the group consisting of 2-trifluoromethoxyaniline, 2-nitroaniline and 4-nitroaniline.

4. Process according to claim 1, wherein the organic solvents used comprise a component selected from the group consisting of aromatic hydrocarbons, halogenated hydrocarbons, alcohols and ethers.

5. Process according to claim 1, wherein sulphur dioxide is used in an amount of from about 1 to 8 mol equivalents, based on the compound of the formula (II).

6. Process according to claim 1, wherein sulphur dioxide is used in an amount of from about 1 to 6 mol equivalents, based on the compound of the formula (II).

7. Process according to claim 1, wherein sulphur dioxide is used in an amount of from about 1.5 to 5 mol equivalents, based on the compound of the formula (II).

8. Process according to claim 1, wherein the alkyl nitrite used comprises a component selected from the group consisting of methyl nitrite, ethyl nitrite and isopropyl nitrite.

9. Process according to claim 1, wherein hydrogen chloride is used in an amount of from about 1 to 4 equivalents.

10. Process according to claim 1, wherein hydrogen chloride is used in an amount of from about 1 to 2 equivalents, based on the compound of the formula (II).

11. Process according to claim 1, wherein the copper catalyst is used in an amount of from about 0.001 to 0.5 mol, per mole of the compound of the formula (II).

12. Process according to claim 1, wherein the copper catalyst is used in an amount of from about 0.005 to 0.1 mol, per mole of the compound of the formula (II).

* * * * *